(12) United States Patent
Angelillo et al.

(10) Patent No.: US 10,881,506 B2
(45) Date of Patent: Jan. 5, 2021

(54) AUDITORY PROSTHESIS FOR MIDDLE-EAR AND RELATED COATING METHOD

(71) Applicant: Sil-Co S.R.L., Pavia (IT)

(72) Inventors: Luigi Angelillo, Naples (IT); Vincenzo Calcagno, Santa Maria a Vico (IT); Maurizio Ettore Maccarini, Pavia (IT); Franco Marabelli, Pavia (IT)

(73) Assignee: SIL-CO S.R.L., Pavia (IT)

( * ) Notice: Subject to any disclaimer, the term of this patent is extended or adjusted under 35 U.S.C. 154(b) by 6 days.

(21) Appl. No.: 16/471,788

(22) PCT Filed: Jan. 10, 2018

(86) PCT No.: PCT/IB2018/050147
§ 371 (c)(1),
(2) Date: Jun. 20, 2019

(87) PCT Pub. No.: WO2018/130947
PCT Pub. Date: Jul. 19, 2018

(65) Prior Publication Data
US 2020/0113675 A1    Apr. 16, 2020

(30) Foreign Application Priority Data
Jan. 10, 2017   (IT) .................. 102017000001834

(51) Int. Cl.
*A61F 2/18*      (2006.01)
*A61L 27/34*    (2006.01)
*A61L 27/56*    (2006.01)

(52) U.S. Cl.
CPC .............. *A61F 2/18* (2013.01); *A61L 27/34* (2013.01); *A61L 27/56* (2013.01); *A61F 2002/183* (2013.01); *A61F 2210/0076* (2013.01); *A61F 2240/001* (2013.01); *A61F 2250/0024* (2013.01); *A61L 2420/02* (2013.01); *A61L 2420/08* (2013.01); *A61L 2430/14* (2013.01)

(58) Field of Classification Search
CPC ... A61F 2/18; A61F 2002/183; A61L 2430/14
See application file for complete search history.

(56) References Cited

U.S. PATENT DOCUMENTS

| 4,859,712 A | 8/1989 | Cox |
| 4,889,744 A | 12/1989 | Quaid |
| 5,814,104 A | 9/1998 | Beoni |
| 2008/0234817 A1 | 9/2008 | Huettenbrink et al. |

FOREIGN PATENT DOCUMENTS

| WO | WO8303350 | 10/1983 |
| WO | WO9715242 | 5/1997 |
| WO | WO2004060428 | 7/2004 |
| WO | WO2006058368 | 6/2006 |
| WO | WO2013138818 | 9/2013 |

*Primary Examiner* — David H Willse
*Assistant Examiner* — Javier G Blanco
(74) *Attorney, Agent, or Firm* — Stetina Brunda Garred and Brucker

(57) ABSTRACT

An auditory prosthesis (1, 101) for middle-ear, in particular for reconstructing the ossicular chain, the auditory prosthesis (1, 101) comprising a portion (2) configured to contact the tympanic membrane, wherein the portion (2) comprises a substrate (4) provided with a coating (6) made of biocompatible silicone, wherein the coating (6) is integrally fixed to the substrate (4) and is adapted to contact, at least partially, the tympanic membrane.

10 Claims, 2 Drawing Sheets

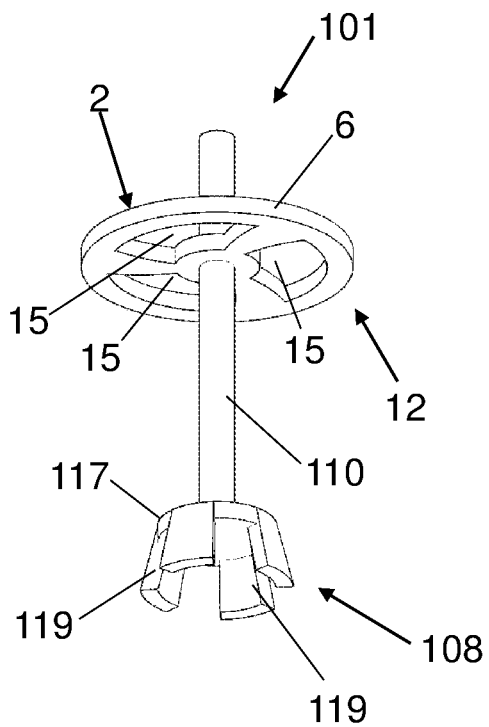
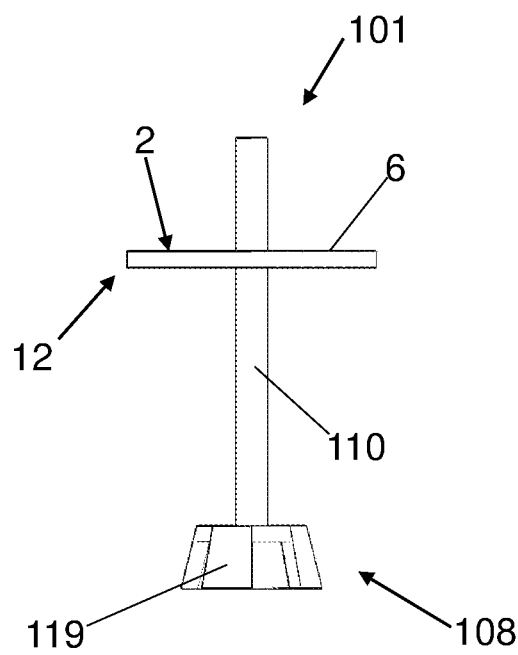
Fig. 5
Fig. 6
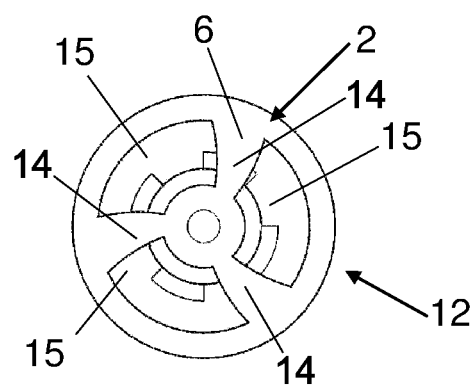
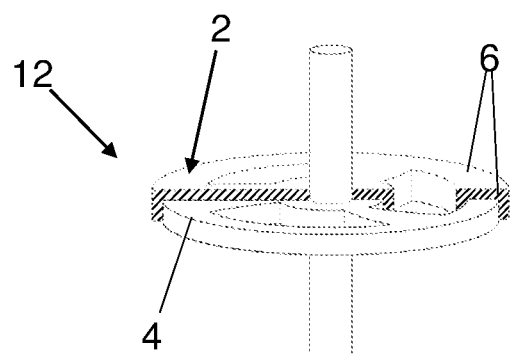
Fig. 7
Fig. 8

AUDITORY PROSTHESIS FOR MIDDLE-EAR AND RELATED COATING METHOD

CROSS REFERENCE TO RELATED APPLICATION(S)

The present application claims priority to PCT International Application No. PCT/IB2018/050147 filed on Jan. 10, 2018, which application claims priority to Italian Patent Application Nos. 102017000001834 filed Jan. 10, 2017, the entirety of the disclosures of which are expressly incorporated herein by reference.

STATEMENT RE: FEDERALLY SPONSORED RESEARCH/DEVELOPMENT

Not Applicable.

FIELD OF THE INVENTION

The present invention relates to an auditory prosthesis for middle-ear, in particular to a prosthesis for reconstructing the ossicular chain, and to a process for obtaining such a prosthesis.

BACKGROUND ART

The middle ear extends from the tympanic membrane to the oval window and contains the bone conduction elements of the hammer, anvil and stirrup. The tympanic membrane is a semi-transparent, thin and oval membrane which separates the outer ear from the middle ear. The hammer head is firmly attached to the medial tympanic membrane.

Ossiculoplasty is defined as the reconstruction of the ossicles chain (stirrup, anvil and hammer). In over 80% of patients, the cause of damage to the ossicles is cholesteatoma or chronic suppurative otitis media. The problems associated with the reconstruction of the ossicular chain in patients with chronic otitis media are very different from those of patients with a dry middle ear and without infections. Acute middle ear infection often results in poor healing, prosthetic extrusion, or both. Some of the problems associated with chronic otitis media include tympanic membrane perforation, Eustachian tube dysfunction, or cochlear deficits. Treatment of patients with cholesteatoma poses a large number of problems. The goals of cholesteatoma removal are to restore a healthy, dry and clean ear, and to improve or maintain hearing. These goals are sometimes mutually exclusive. In particular, a dry and healthy ear may require removal of the posterior external auditory canal. The removal of the canal reduces the volume of the middle ear, which can affect hearing. Trauma or congenital malformations account for most of the remaining causes of bone damage.

The first recorded attempt to re-establish a connection between the tympanic membrane and the oval window, in the case of a missing ossicle, dates back to 1901. Since then, many materials have been used to try to recreate the mechanism of sound conduction in the middle ear, through the replacement or reconstruction of the ossicles, including biological (including auto-grafts of ossicles, cortical bone, teeth and cartilages) and alloplastic materials (implants of non-biological origin).

The most commonly used autologous material is the anvil body, which is often reshaped to fit between the hammer head and the stirrup head. The materials for auto-transplantation are not always available, or, as in the case of patients with cholesteatoma, the ossicle may have microscopic infiltrations of squamous epithelium which preclude such a use thereof. Autografts have some drawbacks, including the lack of availability in chronically sick ears, prolonged operating time to obtain and shape the material, reabsorption and/or loss of rigidity (in particular with the cartilage), and possible fixing to the walls of the middle ear. In addition, an osteitis of the ossicles and the risk of residual cholesteatoma may increase in patients with cholesteatoma.

Human irradiated ossicles and cartilages were first introduced in the 1960s in an attempt to overcome some of the drawbacks of autografts. They can be pre-shaped by the manufacturer, or they can be modeled during the surgery. Since 1986, human materials have been rarely used due to the risk of transmission of infectious diseases (e.g. AIDS, Creutzfeldt-Jakob disease).

Because of the drawbacks of auto-grafting materials and the potential risk of infection of human implants, alloplastic materials are today the most commonly used for ossicular reconstruction. In the late 1960s, materials such as polyethylene or Teflon tubes were used. The reconstruction of the ossicular chain with these materials often resulted in migration, extrusion, penetration into the inner ear or significant reactivity of the middle ear. For these reasons, the use of these solid polymeric substances was finally abandoned.

Stainless steel, titanium and gold are other examples of materials used for the reconstruction of ossicles.

Another material used is Alumina ($Al_2O_3$). This material was popular in Germany and Japan in the 1970s. The implant can be placed on the lower surface of the tympanic membrane without cartilage cover.

Yet other materials used are Bioglass and Ceravital. These do not have extensive use today due to the difficulty in preparing the prosthesis in the operating room and their instability in infected environments.

Hydroxyapatite is another often used material. Hydroxyapatite is the material, among those currently in use, which has shown greater efficacy. However, one of the problems which occur with hydroxyapatite prostheses is related to the duration of the prosthesis itself, which must be replaced after a relatively short time since it was implanted.

In addition, the currently most used auricular prostheses for the reconstruction of the middle ear ossicles, that is, made of titanium and/or hydroxyapatite materials, still exhibit a series of drawbacks. One of the problems which often occur is the extrusion or rejection of the prosthesis, particularly when it is placed in contact with the tympanic membrane.

A further complication is given by the fact that with the current prosthesis it is not always possible to obtain a complete healing of the ear.

The need to overcome the drawbacks of the prior art is therefore felt.

SUMMARY OF THE INVENTION

It is an object of the present invention to provide an auditory prosthesis for the middle ear, in particular for the reconstruction of the ossicles, whose risk of extrusion is eliminated or in any case reduced to the minimum.

It is another object of the present invention to provide such a prosthesis which has a longer service life than the prior art.

It is another object of the present invention to provide such a prosthesis which allows restoring the functionality of the middle ear more effectively than known prostheses.

It is a further object of the present invention to provide such a prosthesis which, in addition to at least one of the aforesaid objects, is simultaneously able to ensure an effective and optimal conduction of sound.

The present invention achieves at least one of these objects, and others which will become apparent in light of the present description, by providing an auditory prosthesis for middle ear, in particular for the reconstruction of the ossicles, the auditory prosthesis comprising a portion configured to contact the tympanic membrane, wherein said portion comprises a substrate provided with a coating made of biocompatible silicone, wherein said coating is integrally fixed to said substrate and is adapted to contact, at least partially, the tympanic membrane.

The coating can consist of a single layer or of two or more superimposed layers.

According to an aspect, the invention also comprises a process for obtaining such a prosthesis. In particular, a process for obtaining such an auditory prosthesis is provided, wherein there are provided:

an auditory prosthesis for middle-ear comprising a part configured to contact the tympanic membrane, said part consisting of said substrate, a base and a corresponding curing agent adapted to be mixed with each other to obtain said biocompatible silicone by cross-linking, said process comprising the steps of:

a1) mixing the base and the curing agent to obtain a mixture;

b) coating at least partially said substrate with said mixture;

c) cross-linking the mixture to solidification in order to obtain the coating, made of biocompatible silicone, of the portion configured to contact the tympanic membrane.

In particular, an auditory prosthesis which is not provided with the coating is coated.

Said part configured to contact the tympanic membrane of the prosthesis to be coated is typically a face of said substrate.

According to one embodiment, the whole prosthesis is coated with biocompatible silicone.

Advantageously, the prosthesis of the invention allows avoiding postoperative complications and extending the average life of the prostheses.

According to an aspect of the invention, in particular when the coating is porous, surface epithelization is favored, stimulating the growth of the tissues inside the pores.

Preferably, each pore has a diameter ranging from 10 to 800 µm, or from 20 to 800 µm, for example from 50 to 100 µm. In a particularly preferred embodiment, in order to achieve optimal epithelization, the pores have a diameter ranging from 10 to 100 µm, preferably from 10 to 50 µm.

Preferably, moreover, the pore density ranges from 0.1 to 0.5, the pore density being the ratio between the volume of all the pores and the total volume of the coating.

Preferably, the coating has a thickness from 20 to 50 µm, more preferably between 25 and 40 µm, even more preferably between 25 and 35 µm.

The above mentioned thickness values are particularly preferred because they do not substantially alter the conduction of sound since the coating is very thin. Moreover, these thickness values derive from an optimization of the process conditions, taking into account that the aim was to obtain a very thin thickness. In particular, with the above thickness values, it is possible to keep the water-soluble pore-forming agent in suspension, avoiding the precipitation thereof. In particular, the pore-forming agent crystals remain in suspension.

The portion adapted to contact the tympanic membrane, in particular with direct contact, is a face of the coating.

Preferably, the portion adapted to contact the tympanic membrane, in particular the above face of the coating, has a surface area between 9 and 10 mm$^2$.

According to further embodiments, the whole prosthesis is provided with the biocompatible silicone coating, one part of which is adapted to contact the tympanic membrane.

According to an aspect of the invention, the wettability of the substrate is favored, thus further promoting the epithelization and growth of the tissues in contact with the prosthesis.

According to an aspect, the biocompatible silicone is preferably Polydimethylsiloxane (PDMS), as it is particularly suitable for biomedical and pharmaceutical applications. The "medical grade" type is particularly preferred as it is non-irritating and non-sensitizing. Furthermore, it is a material which has a relatively low cost.

A further advantage derives from the fact that the biocompatible silicone is non-biodegradable and, consequently, guarantees a longer service life of the prosthesis itself. Moreover, the biocompatible silicone avoids the disadvantageous fixation of the prosthesis with the bone tissue (synostosis), which usually occurs in the case of hydroxyapatite prostheses. Furthermore, the increased epithelization of the tissues in contact with the coating ensures further reducing the degree of extrusion of the prosthesis itself.

Advantageously, a prosthesis for the reconstruction of the ossicles is obtained, which is bio-compatible, stable, safe, easily insertable and capable of producing an excellent transmission of sound.

By way of non-limiting example, when in the present description reference is made to a "compact", or "dense", or "non-porous" layer, it is preferable that the density of the cross-linked silicone is between 0.9 and 1.2 g/cc, preferably between 0.965 and 1.11 g/cc, for example 1.11 g/cc.

The base and the curing agent of a silicone, such as PDMS, are well known to those skilled in the art and typically available on the market.

The dependent claims describe preferred embodiments of the invention.

BRIEF DESCRIPTION OF THE DRAWINGS

Further features and advantages of the invention will become more apparent from the detailed description of preferred, but not exclusive, embodiments of auditory prostheses for middle-ear. Examples of processes with which this prosthesis can be obtained are also described. The description is provided by way of non-limiting example with reference to the accompanying drawings, which are also provided by way of non-limiting example, in which:

FIG. 5 shows a perspective view of another example of auditory prosthesis according to the invention;

FIG. 6 shows a front view of the prosthesis in FIG. 5;

FIG. 7 shows a top view of the prosthesis in FIG. 5;

FIG. 8 shows a perspective view of a part of the prosthesis in FIG. 5, schematized to better illustrate the coating thereof.

The same reference numerals in the figures identify the same or substantially equivalent components.

DETAILED DESCRIPTION OF EMBODIMENTS OF THE INVENTION

With reference to the Figures, an auditory prosthesis 1, 101 for the middle ear is described, in particular for reconstructing the ossicular chain.

The auditory prosthesis 1, 101 comprises a portion 2 configured to contact the tympanic membrane.

The portion 2 comprises a substrate 4 provided with a coating 6 made of biocompatible silicone or silicone elastomer.

The coating 6 is integrally fixed to the substrate 4 and is preferably in direct contact with the substrate 4.

Advantageously, the coating 6 is the part of the auditory prosthesis 1, 101 adapted to contact, at least partially, the tympanic membrane.

The auditory prosthesis 1, 101 of the invention is designed to partially or totally replace the elements which form the ossicular chain of the middle ear and to allow the mechanical conduction of sound from the tympanic membrane to the inner ear.

Figure 1:
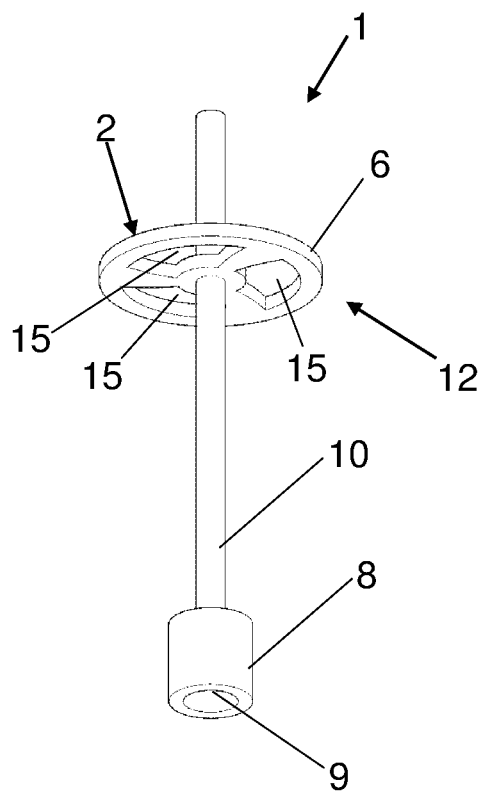
FIG. 1 shows a perspective view of an example of auditory prosthesis according to the invention.
Figure 2:
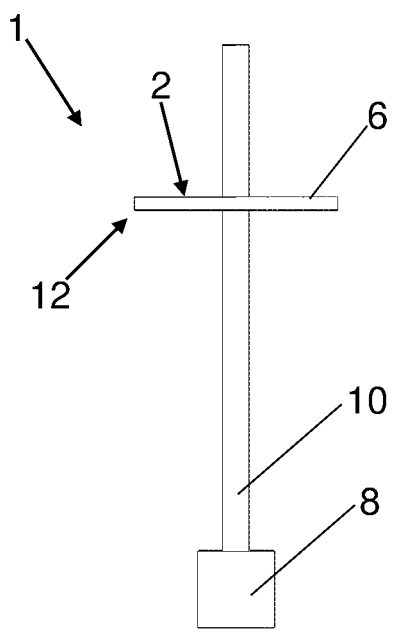
FIG. 2 shows a front view of the prosthesis in FIG. 1.
Figure 3:
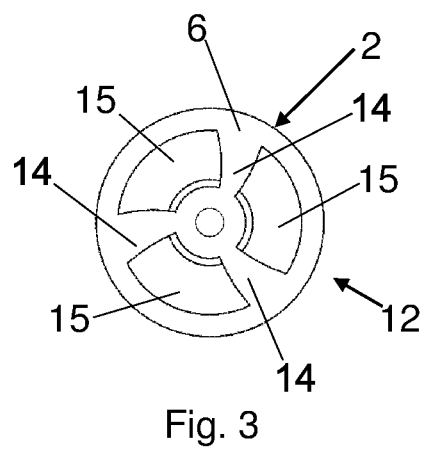
FIG. 3 shows a top view of the prosthesis in FIG. 1.
Figure 4:
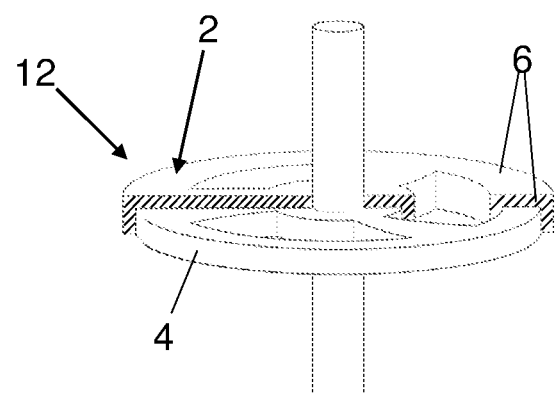
FIG. 4 shows a perspective view of a part of the prosthesis in FIG. 1, schematized to better illustrate the coating thereof.

According to a first embodiment, shown in FIGS. 1 to 4, the invention provides an auditory prosthesis 1 of the TORP (Total Ossicular Replacement Prosthesis) type, designed to replace the entire ossicular chain, in particular the anvil, the hammer and the stirrup.

Typically, the prosthesis 1 comprises an element 8 designed to be connected to the base of the damaged stirrup. The element 8 has substantially the shape of a cylinder, preferably provided with a cavity 9, i.e. a recess. A rod 10 extends orthogonally from the end of the element 8 opposite the end in which the opening of cavity 9 is provided. The rod 10 also has the shape of a cylinder and has an outer diameter smaller than the outer diameter of the element 8. Typically, the axial length of the rod 10 is greater than the axial length of the element 8. Optionally, the prosthesis is adjustable in length, for example the rod 10 can be cut. Optionally, the element 8 and the rod 10 are integral with each other, forming a single, preferably monobloc component.

The prosthesis 1 also comprises an element 12, preferably and substantially discoidal, adapted to contact the eardrum. In particular, the element 12 is configured to replace the hammer. The element 12 has an outer contour which is preferably circular, having an outer diameter greater than the outer diameter of the element 8. Preferably, the outer diameter of the element 12 is the maximum diameter of the whole prosthesis 1. The element 12 is provided with a hole, preferably central or offset with respect to the geometric center defined by the contour of the element 12, in which the rod 10 is inserted. The rod 10 and the element 12 are fixed to each other. Optionally, fixing is done by means of a coupling, for example threaded or insertion coupling. Optionally, it is a fixing which allows adjustment of the position of the element 12 along the rod 10, depending on the patient's anatomy, if such adjustment is envisaged. The element 12 may be arranged such that there is a portion of rod 10 from one side of the element 12 and a portion of rod 10 from the other side of the element 12, or the element 12 may be an end component of the prosthesis.

The element 12 is optionally provided with at least one opening, for example three openings 15, separated by respective portions 14, or segments, which connect the portion surrounding the hole of the element 12 to the contour portion of the element 12.

The element 12 comprises a substrate 4 and a coating 6 of the substrate 4. The substrate 4 and the coating 6 are made of different materials. Preferably, but not exclusively, the substrate 4 is made of titanium or alloys thereof, or hydroxyapatite, or titanium-hydroxyapatite, or porous titanium-hydroxyapatite, or PTFE, or HAPEX, or Nitinol or other metal alloys, gold, silver, stainless steel, Pt, Pd, etc.

The coating 6 is made of a biocompatible silicone, which is preferably PDMS. Preferably, PDMS is of a medical grade type, for example Silastic® MDX4-4210 BioMedical Grade Elastomer, produced by Dow® Corning, or a similar or equivalent product. According to another example, PDMS is of the Sylgard® 184 type.

The coating 6 adheres at least to the surface of the substrate 4 which is distal from the element 8, coating at least this distal surface of the substrate 4. The element 12 has a surface distal from the element 8 which is the portion 2 destined to contact the tympanic membrane. This portion 2 is therefore the surface of the coating 6 which is distal from the element 8.

Optionally, the element 12 is the only element of the prosthesis 1 to be provided, at least on the above mentioned distal surface of the substrate 4, with the coating 6 of biocompatible silicone. The other elements of the prosthesis 1 are made for example of the same material as the substrate 4.

Optionally, only the distal surface of the substrate 4 is covered by the coating 6. Optionally, alternatively, only the distal surface of the substrate 4 and the surface orthogonal thereto of the element 12 are covered by the coating 6. Optionally, alternatively, all the substrate 4 is covered by the coating 6.

Optionally, as a result of the coating process, also a small area of the rod 10 in the vicinity of the element 12 can be covered with biocompatible silicone.

Alternatively, according to one example, both the element 8 and the element 12 are provided with the biocompatible silicone coating. According to another example, the whole prosthesis 1 is provided with the biocompatible silicone coating. In particular, also in these last two examples, a substrate preferably analogous to the substrate 4 is coated with the biocompatible silicone coating.

Preferably, the coating 6 has a thickness ranging from 20 to 1000 μm, or from 50 to 1000 μm, or from 20 to 500 μm, or from 100 to 500 μm, for example the thickness is equal or approximately equal to 20, 25, 30, 35, 40, 45, 50, 100, 150, 200, 250, 300, 350, 400, 450, or 500 μm. It is particularly preferred that the coating 6 has a thickness from 20 to 50 μm, more preferably from 25 to 40 μm, even more preferably from 25 to 35 μm.

Preferably, the thickness is constant or substantially constant. In particular, such a thickness is the distance between the outer surface of the coating and the outer surface of the coated part, i.e. the surface underlying the coating 6.

For example, the thickness is the distance between the surface of the substrate 4 and the outer surface of the coating 6, in particular the distance between the distal surface of the substrate 4 and the distal surface of the coating 6.

In a second embodiment, shown in FIGS. 5 to 8, the invention provides an auditory prosthesis 101 of the PORP (Partial Ossicular Replacement Prosthesis) type, designed to replace the partially damaged part of the ossicular chain. Typically, the damaged part is the anvil and the hammer, while the stirrup is intact.

A difference between the prosthesis 1 of the first embodiment and the prosthesis 101 of the second embodiment is the axial length of the respective rods. In particular, the axial length of the rod 110 is less than the axial length of the rod 10.

Another difference between the prosthesis 1 of the first embodiment and the prosthesis 101 of the second embodiment is the conformation of the respective elements 8 and 108.

Typically, the prosthesis 101 comprises an element 108, designed to be connected to the intact stirrup. The element 108 is formed by a disc-shaped portion 117 from which fins 119 extend, for example four fins 119 separated from one another by an empty space. A rod 110 extends orthogonally from the element 108. In particular, the rod 110 extends from the disc-shaped portion 117, in the opposite direction with respect to the direction of extension of the fins 119. The rod 10 has the shape of a cylinder and has an outer diameter smaller than the outer diameter of the disc-shaped portion 117. Typically, the axial length of the rod 110 is greater than the axial length of the element 108. Typically, the element 108 and the rod 110 are integral with each other, forming a single, preferably monobloc component.

The prosthesis 101 also comprises an element 12, preferably substantially discoidal, adapted to contact the eardrum. The element 12 has an outer contour which is preferably circular, having an outer diameter greater than the outer diameter of the disc-shaped portion 117 of the element 118. Preferably, the outer diameter of the element 12 is the maximum diameter of the prosthesis 101. The element 12 is provided with a hole, preferably central or offset with respect to the geometric center defined by the contour of the element 12, in which the rod 110 is inserted. The rod 110 and the element 12 are fixed to each other. Optionally, fixing is done by means of a coupling, for example threaded or insertion coupling. Optionally, it is a fixing which allows the adjustment of the position of the element 12 along the rod 110, depending on the patient's anatomy, if such adjustment is envisaged. The element 12 may be arranged such that there is a portion of rod 110 from one side of the element 12 and a portion of rod 110 from the other side of the element 12, or the element 12 may be an end component of the prosthesis.

The element 12 is optionally provided with at least one opening, for example three openings 15, separated by respective portions 14, or segments, which connect the portion surrounding the hole of the element 12 to the contour portion of the element 12.

The element 12 comprises a substrate 4 and a coating 6 of the substrate 4. The substrate 4 and the coating 6 are made of different materials. Preferably, but not exclusively, the substrate 4 is made of titanium or alloys thereof, or hydroxyapatite, or titanium-hydroxyapatite, or porous titanium-hydroxyapatite, or PTFE, or HAPEX, or Nitinol or other metal alloys, gold, silver, stainless steel, Pt, Pd, etc.

The coating 6 is made of a biocompatible silicone, which is preferably PDMS. Preferably, PDMS is of a medical grade type, for example Silastic® MDX4-4210 BioMedical Grade Elastomer, produced by Dow® Corning, or a similar or equivalent product. According to another example, PDMS is of the Sylgard® 184 type.

The coating 6 adheres at least to the surface of the substrate 4 which is distal from the element 108, coating at least this distal surface of the substrate 4.

The element 12 has a surface distal from the element 108 which is the portion 2 destined to contact the tympanic membrane. This portion 2 is therefore the surface of the coating 6 which is distal from the element 108.

Preferably, the element 12 is the only element of the prosthesis 101 to be provided, at least on the above mentioned distal surface of the substrate 4, with the coating 6 of biocompatible silicone. The other elements of the prosthesis 101 are made for example of the same material as the substrate 4.

Optionally, only the distal surface of the substrate 4 is covered by the coating 6. Optionally, alternatively, only the distal surface of the substrate 4 and the surface orthogonal thereto of the element 12 are covered by the coating 6. Optionally, alternatively, all the substrate 4 is covered by the coating 6.

Optionally, as a result of the coating process, also a small area of the rod 110 in the vicinity of the element 12 can be covered with biocompatible silicone.

Alternatively, according to one example, both the element 8 and the element 12 are provided with the biocompatible silicone coating. According to another example, the whole prosthesis 1 is provided with the biocompatible silicone coating.

Preferably, the coating 6 has a thickness ranging from 20 to 1000 µm, or from 20 to 500 µm, or from 50 to 1000 µm, or from 100 to 500 µm, for example the thickness is equal or approximately equal to 20, 25, 30, 35, 40, 45, 50, 100, 150, 200, 250, 300, 350, 400, 450, or 500 µm. In a particularly preferred manner, the coating 6 has a thickness from 20 to 50 µm, more preferably from 25 to 40 µm, even more preferably from 25 to 35 µm.

Preferably, the thickness is constant or substantially constant. In particular, such a thickness is the distance between the outer surface of the coating and the outer surface of the coated part, i.e. the surface underlying the coating 6.

For example, the thickness is the distance between the surface of the substrate 4 and the outer surface of the coating 6, in particular the distance between the distal surface of the substrate 4 and the distal surface of the coating 6.

For both the first and second embodiments, the coating 6 may have different features. In particular, each of the following coating features is a variant of the first and second embodiments, respectively.

According to a first variant, the coating 6 is compact, or dense, meaning that it is substantially non-porous.

According to a second variant, the coating 6 is porous. In fact, in this variant, the coating 6 has a plurality of pores (not shown). Preferably, the pore density is between 0.1 and 0.5, for example 0.2, expressing the porosity as Volume of all pores/Total volume of coating (Vpores/Vtot). By way of example, by expressing the pore density as the number of pores per unit volume, the pore density is about $3*10^5$ pores/cm$^3$, for example when the coating thickness is about 50 µm. Preferably, the pores have a diameter ranging from 10 to 800 µm or from 20 to 800 µm, for example from 50 to 100 µm. In a particularly preferred embodiment, the pores have a diameter ranging from 10 to 100 µm, preferably from 10 to 50 µm.

According to a third variant, the coating consists of two layers, a first layer of which is compact, i.e. non-porous, and is in direct contact with the substrate 4. The second layer, which is the outermost, is porous and is superimposed on the first layer. The second layer is therefore apt to contact the tympanic membrane. Preferably, the pore density of the second layer is between 0.1 and 0.5, for example 0.2, expressing the porosity as Volume of all pores/Total volume of coating (Vpores/Vtot). By way of example, by expressing the pore density as the number of pores per unit volume, the pore density of the second layer is about $3*10^5$ pores/cm$^3$, for example when the thickness of the second layer is about 50 µm. Preferably, the pores of the second layer have a diameter ranging from 10 to 800 µm or from 20 to 800 µm, for example from 50 to 100 µm. It is particularly preferred that the pores have a diameter ranging from 10 to 100 µm, preferably from 10 to 50 µm.

It should be understood that the description of the two embodiments of an auditory prosthesis and of the variants thereof has been provided as an example and not a limitation. In particular, those skilled in the art are able to understand that the specific geometrical conformation of the elements 8, 108 and/or of the rods 10, 110 and/or of the element 12 may be different from that shown and described, while obtaining a prosthesis of the TORP or PORP type, depending on the specific case.

After providing an exemplary description of auditory prostheses according to the invention, non-limiting examples are described below to make a prosthesis according to the invention, in particular according to the two embodiments and variants thereof described above.

A process is in fact provided in which there are provided:
an auditory prosthesis for middle-ear comprising a portion configured to contact the tympanic membrane, said portion consisting of said substrate,
a base and a corresponding curing agent adapted to be mixed with each other to obtain said biocompatible silicone by cross-linking.

The process comprises the steps of:
a1) mixing the base and the curing agent to obtain a mixture;
b) coating at least partially the substrate 4 with such a mixture;
c) cross-linking the mixture to solidification in order to obtain the coating 6, made of biocompatible silicone, of the portion 2 configured to contact the tympanic membrane.

In other words, an auditory prosthesis which is not provided with the coating 6 is a starting material. In particular, with reference to the description of the prosthesis 1, 101 provided above, the element 12 of the starting auditory prosthesis consists exclusively of the substrate 4. During the process of the invention, the element 12 can be optionally separated from the rest of the prosthesis 1, 101, or in any case can be coated separately and then assembled with the rest of the prosthesis.

It is also possible to provide for further elements of the prosthesis being coated with the mixture.

The biocompatible silicone, or elastomer, is preferably Polydimethylsiloxane, more preferably of the medical grade type, for example Silastic® MDX4-4210.

With reference to step a1), when, for example, Silastic® MDX4-4210 is used, the base and the corresponding curing agent are homogeneously mixed in a ratio of preferably about 10:1, base:curing agent. However, this ratio may be varied to adjust the stiffness of the solidified elastomer. For example, this ratio can range from 10:4 to 40:1, base:curing agent, preferably from 10:2 to 20:1 base:curing agent. In a particularly preferred manner, the base:curing agent ratio is about 10:1.

Silastic® MDX4-4210 is a medical grade silicone elastomer used to make PDMS (polydimethylsiloxane). The kit consists of two liquid components, i.e. the base and the curing agent. Typically, the viscosity is about 5000 cSt for the base alone and about 3500 cSt when the base and the curing agent are mixed in a 10:1 ratio.

The base-curing agent mixture is also called a pre-polymer. Optionally, in particular when a solvent is not used, after step a1) a degassing step of the mixture is provided, which can be carried out for example by applying a slight depression to the mixture, or by centrifugation at low speeds (for example 2000 rpm for 1 minute).

With reference to step b), the substrate 4 can be coated by immersion in the base-curing agent mixture. Alternatively, the base-curing agent mixture can be homogeneously sprayed on the part of substrate 4 to be coated, by means of suitable spraying means. Alternatively, the mixture can be deposited by means of a spin coater.

With reference to step c), cross-linking, also called curing step, can be carried out at room temperature, for example at about 25° C., or at a higher temperature, for example up to 190° C. When cross-linking is conducted at a temperature higher than the room temperature, heating means are provided, for example a stove. Optionally, the stove can be connected to suction means, for example a vacuum pump, to create vacuum inside the stove during the cross-linking step, so as to eliminate any vapors produced by the PDMS itself and/or by the possible solvent.

Typically, the temperature at which cross-linking is conducted determines the duration of cross-linking to obtain a solid elastomer. For example, when the temperature is about 25° C., the duration of the cross-linking step is preferably about 48 hours. The time can be reduced up to about 10 minutes by working at higher temperatures.

Once the mixture is cross-linked to solidification, the coating 6 is obtained.

According to a variant, the above process involves the use of a solvent, in particular a solvent for the base or for the base-curing agent mixture. By way of example, the solvent is a volatile organic solvent, for example a short-chain aliphatic solvent, such as hexane, pentane, n-heptane, cyclohexane and the like; or the solvent is tert-butyl alcohol, ether, trichlorethylene, dimethoxyhexane, xylene, toluene, benzene, chloroform, THF. Preferably, the solvent is hexane.

In this variant, the process comprises the step of:
a2) diluting the base-curing agent mixture by means of such a solvent to obtain a diluted mixture. Step a2) is conducted between step a1) and step b).

The use of the solvent to dilute the base-curing agent mixture is advantageous because it allows reducing the viscosity of the mixture, so as to facilitate the obtainment of a coating with the desired thickness. Furthermore, the dilution of the mixture facilitates the obtainment of a constant thickness.

The ratio between mixture and solvent ranges preferably from 10:1 to 1:10 (mixture:solvent), for example between 10:5 and 5:10.

For example, when the solvent is hexane and the silicone is PDMS, the ratio of the pre-polymer PDMS mixture to hexane can range from 10:1 to 1:10 (mixture:solvent), for example from 10:5 to 5:10.

One way to change the thickness is to adjust the base:solvent ratio. Typically, the stiffness of the coating can be adjusted by varying the ratio of the base to the curing agent (which is preferably comprised between a 10:4 ratio and a 40:1 ratio, more preferably equal to about 10:1) and/or increasing the time necessary to cure the pre-polymer, preferably in a range of 10 minutes to 48 hours.

In step b) the substrate 4 is coated with the diluted mixture, and in step c) the diluted mixture is cross-linked to solidification of the mixture and evaporation of the solvent.

According to a variant, both when solvent dilution is provided and when the dilution is not provided, the coating is made microscopically porous, in particular the surface of the coating is made microscopically porous. Advantageously, a porous coating 6 increases the adhesion between prosthesis 1, 101 and tympanic membrane.

In this variant, a water-soluble pore-forming agent is provided, for example a salt, such as sodium chloride, a sugar and the like.

A solution is also provided for the dissolution of the pore-forming agent which is preferably a solution comprising water or consisting of water. For example, a solution of water with an alcohol, e.g. a water-ethanol mixture, can be provided. Preferably, a 20% ethanol water-ethanol mixture is provided.

According to this variant, the process comprises the following step, carried out either between steps a1) and b) or between steps a2) and b):

a3) adding the pore-forming agent to the mixture or to the diluted mixture in order to obtain a suspension.

In step b) the substrate 4 is coated with the suspension, and in step c) the suspension is cross-linked to solidification.

After step c), the following step is further provided:

d) dissolving the pore-forming agent present in the cross-linked suspension by means of said solution, whereby the biocompatible silicone coating 6 obtained is porous.

The pore-forming agent, typically in the form of crystals, is therefore added to the pre-polymer mixture, diluted or undiluted, before the mixture is cured. The dimensional intervals of the crystals, which substantially correspond to the pore size, are preferably the following: 10-100 µm, or 10-50 µm, or 20-50 µm, or 50-100 µm, or 100-200 µm, or 200-300 µm, or 300-500 µm, or 500-800 µm.

For example, with reference to sodium chloride for descriptive purposes, in order to obtain a regular porosity of the coating and pores of the desired size, the sodium chloride crystals are preventively reduced in size by means of Blender or Mortar and the desired dimensions of the crystals are selected using micrometer mesh sieves.

The pore-forming agent crystals thus obtained are mixed together with the pre-polymer before the latter is cured.

In general, amounts of pore-forming agent may vary depending on the desired degree of porosity, preferably from 10 to 200% by weight of pore-forming agent, for example between 25% and 80% by weight of pore-forming agent. After the cross-linking step, the pore-forming agent is dissolved and washed away, by immersing the prosthesis in the above mentioned solution and then letting it dry in air or in a stove.

Example: In an exemplary procedure, the pre-polymer mixture is prepared by adding and homogeneously mixing the base, the curing agent and the hexane with a 10:1:8 weight ratio (base:curing agent:hexane). Once a homogeneous mixture is obtained, the pore-forming agent, in particular sodium chloride, is added optionally to it, in a 2:1 ratio (base:pore-forming agent), in the form of crystals having a size range of 50-100 µm, obtaining an opalescent homogeneous suspension. The coating is made by partially immersing the prosthesis in the mixture in order to create a continuous surface film. The part mainly involved in the coating is that involving a direct contact with the tympanic membrane. In particular, the distal surface of the substrate 4 and the orthogonal surfaces to the distal surface of the substrate 4 are coated (see, for example, FIGS. 4 and 8). It should be noted that, for illustrative purposes, in FIGS. 4 and 8, only a part of the coating 6 is shown, which is shown partially sectioned.

Once the substrate 4 has been coated, the cross-linking step, or polymerization, is carried out by inserting the prosthesis in a stove at 70° C. for 2 hours and 190° C. for a further 2 hours. The prosthesis is then allowed to cool and is immersed in an ethanol solution in 20% water, in order to completely dissolve the pore-forming agent. The prosthesis is then dried in a stove at 60° C. for 1 hour.

According to another variant, a process is performed to obtain an auditory prosthesis, the coating of which consists of two layers, a first layer of which is compact or dense, i.e. non-porous, and is in direct contact with the substrate 4. The second layer, which is the outermost, is porous and is superimposed on the first layer. The second layer is therefore adapted to contact the tympanic membrane.

Advantageously, the first and second polymer layers have different physical properties. In this variant, the method includes making a first coating layer with the pre-polymer without a pore-forming agent, so as to obtain a first non-porous layer. This first coating layer, after the related cross-linking step in a stove, follows a second coating operation to produce a second coating layer obtained by using a mixture with the pore-forming agent, so as to obtain a porosity of the second layer, which is the outermost.

Optionally, for all the variants of the process it is possible to provide, after cross-linking the coating, a step of removing the unreacted components, i.e. the pre-polymer and the curing agent, also referred to as oligomers, in order to further increase the stiffness of the coating and its biocompatibility. This removal is obtained by immersing the coated part in a hexane solution, preferably for a period of time ranging from 30 minutes to 2 hours, followed by immersion in water, preferably for a period of time ranging from 30 minutes to 4 hours.

Optionally, for all the variants of the process it is possible to provide, after cross-linking the coating, a surface silanization step of the coating, carried out in wet, that is, by means of a suitable solution, or by plasma treatment; and/or it is possible to provide a functionalization of the surface with biomolecules, that is, by binding biomolecules, of one or more types, with silicone. The term "biomolecule" means any organic substance or molecule having functional groups capable of binding to silicone. Examples of biomolecules are polyamino acids, peptides, proteins, aptamers or others.

The wet silanization is obtained for example by immersing the coated part in an acidic solution of hydrogen peroxide for 20 minutes. The solution is prepared with a 1:1:5 volumetric ratio of $H_2O_2$:HCl:$H_2O$ (where $H_2O_2$ and HCl are 30% and 37% aqueous solutions, respectively). As a consequence of silanization, the coating takes a hydrophilic interface and the surface wettability is increased.

Typically, the wettability obtained by silanization is short-lived if the surface is exposed to air. Therefore, it is preferable to store the prosthesis having a surface which has undergone the silanization, in a polar solution (such as water, saline solution, ethanol, a water/ethanol mixture or the like), so as to make the silanization treatment permanent.

Furthermore, the silanization treatment can be conveniently used to cover the surface with a polyelectrolyte, such as with a polylysine solution, which has the purpose of increasing cell adhesion and, therefore, epithelization. The silanization can also be used to bind small biomolecules to the surface so as to stimulate or increase the epithelization of the coating.

The invention claimed is:

1. An auditory prosthesis for middle-ear comprising a portion configured to contact a tympanic membrane,
   wherein said portion comprises a substrate-provided with a coating,
   wherein said coating is
      integrally fixed to said substrate and is
      adapted to contact, at least partially, a tympanic membrane;

characterized in that
the coating is made of biocompatible silicone and in that the coating is silanized,
wherein said biocompatible silicone is a Polydimethylsiloxane (PDMS).

2. The auditory prosthesis according to claim 1, wherein a thickness of said coating ranges from 50 μm to 1000 μm, or from 100 μm to 500 μm.

3. The auditory prosthesis according to claim 1, wherein the coating has a thickness ranging from 20 μm to 50 μm.

4. The auditory prosthesis according to claim 3, wherein said thickness ranges from 25 μm to 40 μm.

5. The auditory prosthesis according to claim 1, wherein said coating is porous, having a plurality of pores.

6. The auditory prosthesis according to claim 5, wherein each pore of said plurality of pores has a diameter ranging from 20 μm to 800 μm.

7. The auditory prosthesis according to claim 5, wherein each pore of said plurality of pores has a diameter ranging from 10 μm to 100 μm.

8. The auditory prosthesis according to claim 7, wherein said diameter ranges from 10 μm to 50 μm.

9. The auditory prosthesis according to claim 5, wherein a pore density of said plurality of pores ranges from 0.1 to 0.5, said pore density being the ratio between the volume of the plurality of pores and the total volume of the coating.

10. The auditory prosthesis according to claim 1, wherein said coating comprises two layers, of which
   a first layer is compact and in direct contact with said substrate, and
   a second layer is porous,
   wherein said second layer is:
      superimposed on the first layer,
      adapted to contact the tympanic membrane, and
      has a plurality of pores.

* * * * *